United States Patent [19]

Ainpour

[11] Patent Number: 4,526,579
[45] Date of Patent: Jul. 2, 1985

[54] METHOD FOR GRAFT COPOLYMERIZATION TO NATURAL RUBBER ARTICLES

[75] Inventor: Parviz R. Ainpour, Groton, Conn.

[73] Assignee: Pfizer Inc., New York, N.Y.

[21] Appl. No.: 505,572

[22] Filed: Jun. 17, 1983

[51] Int. Cl.$^3$ .................. A61M 25/00; C08L 51/04
[52] U.S. Cl. ................................ 604/265; 525/244; 525/285; 525/301; 525/333.1; 525/386; 604/266
[58] Field of Search ........... 525/244, 285, 301, 333.1, 525/386; 604/265, 266

[56] References Cited

U.S. PATENT DOCUMENTS

| | | | |
|---|---|---|---|
| 3,566,874 | 3/1977 | Shepherd et al. | 128/349 |
| 4,347,341 | 8/1982 | Bartl et al. | 525/285 |
| 4,382,128 | 5/1983 | Li | 525/285 |
| 4,459,318 | 7/1984 | Hyans | 604/266 |

OTHER PUBLICATIONS

"Block and Graft Copolymerization", R. J. Ceresa, Editor, Wiley and Sons, New York, 1973, pp. 47–97.
Burfield et al., European Polymer, J., 14, 799 (1978).
"The Vanderbilt Rubber Handbook," R. T. Vanderbilt Company, Inc., N.Y.C. pp. 154–156, (1958).

Primary Examiner—Allan M. Lieberman
Attorney, Agent, or Firm—Charles J. Knuth; Albert E. Frost; Paul D. Thomas

[57] ABSTRACT

A process for grafting a hydrophilic polymer of a carboxylic acid or a salt thereof onto the surface of a natural rubber article by contacting said article in reaction inert solvent with a vinyl carboxylic acid anhydride and initiator, and subsequent washing and hydrolysis of anhydride groups to carboxylate groups and an article when prepared by the invention process.

16 Claims, No Drawings

METHOD FOR GRAFT COPOLYMERIZATION TO NATURAL RUBBER ARTICLES

BACKGROUND OF THE INVENTION

1. Field of the Invention

A process for graft copolymerization of certain alpha-vinyl carboxylic acid anhydride monomers onto the surface of a natural rubber article and subsequent hydrolysis of anhydride to form hydrophilic carboxylate groups, and a rubber article formed by said process.

2. Description of the Prior Art

The synthesis and properties of block and graft copolymers, including grafting onto natural rubber has been reviewed recently in "Block and Graft Copolymerization", R. J. Ceresa, Editor, Wiley and Sons, New York, 1973, p. 47–97. A kinetic study of graft copolymerization of methacrylamide to latex rubber emulsions has been reported by Burfield et al., European Polymer J., 14, 799 (1978). The final product obtained by prior graft polymerization methods in which the graft is chemically bonded to rubber was a filterable crumb which cannot be readily processed to provide rubber articles such as, for example, gloves, sheet, tubing and catheters. Unsuccessful attempts to graft maleic anhydride onto natural rubber crumb have been discussed by Casale et al., Rubber Chem. Technol., 44, 534 (1971).

Sheperd et al., U.S. Pat. No. 3,566,874 disclose a method for coating natural rubber catheters with an hydrophilic acrylate or methacrylate polymer. The coating reduces the irritation and infection normally accompanying the use of catheters. The catheter is dipped into a prepolymerized mixture of monomers (e.g., hydroxyethyl methacrylate, ethylene glycol dimethacrylate) and then heat cured. Since the patent states that adhesion would not occur if the cross-linking agent (e.g. ethylene glycol dimethacrylate) is omitted, it is unlikely that the coating is chemically bonded to the rubber. Therefore, this process provides a surface coating, not chemically bonded to the substrate. Such coatings lack dimensional stability and tend to crack upon aging.

SUMMARY OF THE INVENTION

The present invention provides a novel process for grafting a hydrophilic polymer of a vinyl carboxylic acid or its salt onto the surface of a natural rubber article which comprises the steps of (a) contacting said rubber article, in the presence of a reaction inert organic solvent, with from about 0.1 to 100 parts by weight, based on weight of rubber article, of an anhydride of said vinyl carboxylic acid and from about 0.4 to 10%, especially from about 2 to 6%, of initiator, based on weight of acid anhydride, at a temperature of from about 50° to 150° C., (b) washing the resulting rubber article with a water miscible solvent to remove unreacted monomer, polymeric vinyl carboxylic anhydride not chemically bonded to the rubber article, and (c) hydrolysis of the washed article to convert carboxylic anhydride groups to carboxylic acid groups or a salt thereof.

Preferred vinyl carboxylic acid anhydrides for use in the invention process are those selected from the group consisting of maleic, acrylic, methacrylic, itaconic and citraconic acid anhydride. An especially preferred acid anhydride is maleic anhydride.

Preferred rubber articles for the invention are in the form of a sheet, glove or tube. An especially preferred tube is a catheter.

The invention further provides a natural rubber article having a hydrophilic surface chemically bonded thereto when prepared by the above process of the invention.

The invention process provides novel, hydrophilic rubber articles which have reduced frictional resistance to human skin and are more compatible with it. Due to these advantageous properties, catheters prepared by the invention process are less likely to induce irritation or cause infection in normal usage.

DETAILED DESCRIPTION OF THE INVENTION

The invention process is carried out by first contacting the rubber article with a monomeric acid anhydride of a polymerizable vinyl carboxylic acid in the presence of a reaction inert solvent and an initiator. The polymerizable monomeric acid anhydride is preferably a member selected from the group consisting of maleic anhydride, itaconic anhydride, citraconic anhydride, acrylic anhydride or methacrylic anhydride.

Examples of natural rubber articles which are advantageously grafted by the invention process are sheeting, gloves, tubing including catheters and cannulas.

A reaction inert solvent which is suitable for use in the instant process is one which, under the conditions employed, dissolves at least substantial portions of the monomeric acid anhydride and initiator employed, has no significant detrimental effect on the starting rubber article or product and does not adversely interfere with the polymerization of monomer. Examples of such reaction inert solvent include benzene, toluene, xylene, chlorobenzene, bromobenzene, pyridine, anisole, chloroform, 1,2-dibromoethane and perchloroethylene. Particularly preferred such solvents are chlorobenzene and bromobenzene, especially the former.

The initiators employed in the invention process may be any of the well known substances used in the art of polymerization which serve as a source of radicals to initiate vinyl polymerization. Examples of suitable initiators are t-butyl peroctoate, benzoyl peroxide, isopropyl percarbonate, methylethyl ketone peroxide, cumene hydroperoxide and dicumyl peroxide. The initiator is employed in an amount which can vary from about 0.05% up to about 10% or more, based on the weight of monomeric acid anhydride. However, a preferred level of initiator is from about 0.4 to 10% and especially from about 2 to 6% based on the weight of acid anhydride.

An especially preferred initiator is t-butyl peroctoate which is typically employed at a level of from 2-6% based on the weight of acid anhydride.

While the graft copolymerization process of the invention can be carried out over a wide range of temperature a preferred temperature is in the range of from about 50° to 150° C. An especially preferred temperature is from about 90° to 110° C.

In the first step of the invention process graft copolymerization of the vinyl acid anhydride to the surface of the rubber article takes place to a substantial extent. However, not all of the vinyl monomer present is bonded to the rubber surface. A portion of the monomer ordinarily undergoes homopolymerization to form a polymeric anhydride and some of the unreacted monomer may remain after polymerization is terminated. Therefore, in the second step of the invention process the rubber article is washed to remove any by-products and unreacted starting materials. The washing is preferably carried out by means of a water miscible solvent. Examples of water miscible solvents for use in this step include acetone, methylethyl ketone, methanol, ethanol, isopropanol, acetonitrile, acetic acid, propionic acid, ethylene glycol, 1,2-dimethoxyethane, 2-methoxyethanol, dimethylformamide, dimethylsulfoxide and mixtures thereof. Particularly preferred water miscible solvents for this step are acetone and ethanol, and acetone is especially preferred.

After washing the rubber article to substantially free it from starting materials and by-products, the resulting grafted copolymer still contains carboxylic anhydride groups. In order to convert the anhydride groups to carboxylic acids or salts thereof, the washed rubber article is subjected to hydrolysis conditions. Preferably, the hydrolysis is carried out under aqueous alkaline conditions known in the art to convert carboxylic acids to carboxylate salts. Preferred alkaline reagents for carrying out this step are the alkali metal and alkaline earth hydroxides, e.g. lithium, sodium, potassium, barium or calcium hydroxides. Particularly preferred are the alkali metal hydroxides, especially sodium hydroxide for reasons of efficiency and economy.

When grafted rubber articles containing free carboxylic acid groups are desired, the salt obtained by hydrolysis, above, is acidified, e.g. by reacting it in dilute aqueous or alcoholic hydrochloric acid.

An especially preferred hydrolysis system to convert acid anhydride groups bonded to a rubber article to carboxylate salts employs sodium hydroxide in the presence of aqueous dimethylformamide or aqueous dioxane as solvent. Typically, the rubber article is immersed in one of the above aqueous solvents and an excess of dilute aqueous alkali metal hydroxide, e.g. sodium hydroxide, is added and the mixture stirred overnight at ambient temperature. The rubber article is then removed, washed well with water and dried.

When the rubber article employed in the invention process is rubber tubing, the graft can be applied to the internal wall (lumen) only, to the external surface only, or to both. When only the lumen is grafted, the reaction mixture containing the monomeric anhydride and initiator in reaction inert solvent is circulated through the lumen, typically by means of a suitable pump, while the tube is immersed in the same solvent maintained at the reaction temperature. When the polymerization is terminated, the resulting rubber tube is carried through the remaining steps of the invention process as previously described.

The invention process provides a method for surface grafting to natural rubber articles without causing degradation of the rubber. When the grafted rubber articles prior to the hydrolysis step are analyzed by Attenuated Total Reflectance/Infrared (ATR/IR) Spectroscopy, the presence of anhydride bonds is confirmed. Similarly, the presense of carboxylate salt and absence of anhydride is evidenced by ATR/IR spectroscopy after the rubber article has been subjected to the hydrolysis step of the invention process.

When the article grafted by the invention process is a rubber glove, the difference between the grafted and ungrafted glove is readily apparent when a human hand is inserted into it. The grafted glove goes onto the hand, and is removed from it, with substantially less frictional resistance than is offered by a similar, but untreated glove.

The rubber articles grafted by the invention process are stable to storage under normal conditions for many months, e.g. from 24 to 36 months, or longer, without significant change in properties. The grafted articles are also stable to prolonged soaking in boiling water as verified by ATR/IR spectroscopy.

The invention is further illustrated by the following examples wherein, unless otherwise stated, all percentages are by weight. All temperatures are in degrees Centigrade.

All chemicals and solvents employed are reagent grade materials purchased from commercial sources.

EXAMPLE 1

Grafting Maleic Anhydride to Latex Sheets, and Hydrolysis to Carboxylate

In a 500 ml resin kettle equipped with condenser, thermometer and gas inlet was placed 300 ml chlorobenzene and three pieces (each $2 \times 2.5$ cm, about 0.3 g) latex rubber sheet having a thickness of 25 mil (0.0635 cm). The sheets had previously been thoroughly washed with a detergent solution and allowed to air dry. The resulting mixture was heated to 100° C. under a nitrogen atmosphere. In a separate flask, 10 g of maleic anhydride, 0.86 g of a 1:1 by weight mixture t-butyl peroctoate in mineral spirit (L-PMS, Lucidol Division, Pennwalt Corp.), 28 ml chlorobenzene and 16 ml acetone are agitated until the maleic anhydride dissolved. The solution is purged with nitrogen and transferred to a dropping funnel and added dropwise to the resin kettle over 20 minutes. After the addition is complete, the mixture is stirred at 100° C. for 90 minutes. The rubber sheets are removed from the kettle, washed three times in a 100 ml beaker with acetone, and dried in a vacuum oven at 60° C. Upon analysis by ATR/IR spectroscopy the sheets showed absorption bands at 1850 and 1770 $cm^{-1}$ (anhydride).

One of the sheets was immersed in a mixture of 80 ml dimethylformamide, 20 ml 1% (w/w) sodium hydroxide solution and the mixture allowed to stir overnight. The sheet was then removed, washed with deionized water and dried under vacuum at 60° C. ATR/IR spectroscopy of the sheet indicated disappearance of anhydride bands and new bands at 1650, 1550 and 1380 $cm^{-1}$ which confirmed the conversion of anhydride to carboxylate anion.

As measured by the weight of substrate before and after the above treatment the level of grafting of polymaleate salt was found to be 1.5 $mg/cm^2$.

Contact angle measurements and calculation of critical surface tension (gamma$_c$) were carried out by standard methods, see, e.g., D. Lyman et al., *Trans. Amer. Soc. Artificial Internal Organs*, 11, 301–306 (1965) and references therein. The results below show that the treated rubber sheet is markedly more hydrophilic and has reduced frictional resistance upon contact with skin than the untreated control rubber sheet.

| Sample | gamma$_c$ (ergs/cm$^2$) |
|---|---|
| Untreated rubber sheet (control) | 33.2 |
| Rubber sheet of above Example | 62 |

EXAMPLE 2

The procedure of Example 1 was repeated but employing three latex rubber sheets (each $2 \times 2.5$ cm, about 75 mg) having a thickness of 5 mil (0.0127 cm) and employing a 30 minute reaction time (after addition of monomer, initiator solution in 5 minutes). The hydrolysis step was carried out in a mixture of 70 ml dioxane, 30 ml 1% (w/w) sodium hydroxide solution. ATR/IR analysis of the hydrolyzed sheets showed bands at 1650, 1550 and 1380 cm$^{-1}$.

By difference in weight of the rubber sheets before and after grafting, the level of grafting was found to be 0.1 mg/cm$^2$.

EXAMPLE 3

In a two liter resin kettle equipped with condenser, thermometer and gas dispenser was added 800 ml chlorobenzene and the system purged with nitrogen while heating to 100° C. A latex rubber surgical glove (11.5 g) which had been thoroughly cleaned in a 1% detergent solution and dried, was placed in the kettle and from an addition funnel was added over five minutes a solution of 30 g maleic anhydride, 2.5 g of 1:1 (w/w) t-butyl peroctoate in mineral oil, 48 ml acetone and 84 ml chlorobenzene, while nitrogen is purging the system. The mixture is stirred for 20 minutes at 100° C. and then cooled by means of an ice-bath, while slowly adding 500 ml acetone. When the internal temperature reached 35° C., the solution was decanted and the glove washed in a beaker with 3×500 ml acetone. The glove was then immersed in a mixture of 350 ml dioxane and 150 ml 1% (w/w) sodium hydroxide solution and soaked for 24 hours at ambient temperature. The glove is then removed from the alkali liquid, washed with deionized water and dried. ATR/IR spectroscopy: 1650, 1550, 1380 cm$^{-1}$.

EXAMPLE 4

Lumenally Grafted Latex Tubing

In this method only the internal wall of the rubber tubing was grafted by continuously cycling the reaction mixture through the solvent-swollen tubing by means of a suitable rotary fluid metering pump*.

*FMI pump No. A09385, Fluid Metering Inc., Oyster Bay, N.Y. 11771.

Two five-liter resin kettles were employed, one as a reaction flask (A) and the other (B) containing the tubing. The pump inlet was connected to flask (A) and the outlet led to the tubing contained in flask (B). The other end of the tubing was connected to a return tube to the reaction flask (A). All external connections between the pump and flasks (A) and (B) were glass tubing with rubber tubing connectors where necessary. In this manner the reaction mixture was circulated through a 12 foot (366 cm) section of latex rubber tubing of 0.25 inch (0.635 cm) outside diameter, 0.0625 inch (0.159 cm) wall thickness, coiled inside flask (B). This flask also contained 3 liters of chlorobenzene and was purged continuously with nitrogen.

In flask (A) was added 900 ml chlorobenzene and the pump started to circulate the solvent through the tubing in flask (B) while heating both flasks to 100°-105° C.

In a separate flask was mixed 84 ml chlorobenzene, 30 g maleic anhydride, 2.5 g 1:1 (w/w) t-butyl peroctanoate/mineral oil (L-PMS) and 48 ml acetone until the anhydride was dissolved. The mixture was flushed well with nitrogen, transferred to a dropping funnel mounted on flask (A) and the solution was added to the reaction flask at 105° C. over three minutes. The reacting mixture was circulated through the tubing at 105° C. for 30 minutes. The entire system was cooled, the tubing removed from the chlorobenzene and soaked in an acetone bath for 30 minutes, then acetone was pumped through the immersed tubing for two hours. The tubing was drained of acetone, filled with a 70/30 (v/v) solution of dioxane/1% (w/w) sodium hydroxide solution and soaked in 2 liters of the same alkaline solution. After soaking for 24 hours the tubing was removed, drained, washed thoroughly with deionized water, dried in vacuo, and its grafted lumen examined by ATR/IR spectroscopy. The presence of grafts were confirmed by absorption bands at 1650, 1550 and 1380 cm$^{-1}$.

EXAMPLE 5

The procedures of Examples 1–4 are repeated but using itaconic anhydride in place of maleic anhydride, benzoyl peroxide as initiator at a level of from 0.4% to 10% of the weight of itaconic anhydride, and bromobenzene as solvent at 80°–150° C. for two hours. The grafted rubber articles are then washed with ethyl alcohol for one hour and the anhydride saponified in 1N alcoholic potassium hydroxide to provide the corresponding hydrophilic grafted rubber articles.

EXAMPLE 6

When the above procedures are repeated but employing acrylic anhydride, methacrylic anhydride or citraconic anhydride as monomer at levels of from 0.1 to 100 parts by weight of anhydride monomer per part by weight of rubber article, the results are substantially the same.

EXAMPLE 7

When the procedure of Example 1 is repeated but employing the following initiators at levels of from 2 to 6% in place of t-butyl peroctoate used therein, similar results are obtained: Isopropyl percarbonate, methylethyl ketone peroxide, cumene hydroperoxide, dicumyl peroxide. The grafting step is carried out at a temperature of from 50°–150° C.

EXAMPLE 8

In a five liter resin kettle containing 2.5 liters bromobenzene is placed a 10 meter length of 2.5 mm diameter rubber tubing. A vacuum is applied to one end of the tubing to suck solvent into it until substantially full. The tubing and solvent are heated to 100° C. for one hour under a nitrogen atmosphere.

In a separate flask is placed a mixture of 100 g citraconic anhydride, 1.0 g isopropyl percarbonate, 50 ml bromobenzene and 25 ml methylethyl ketone. After warming to affect solution, the mixture is added dropwise at 95° C. over ten minutes to the flask containing the tubing. The mixture is heated at 90°–110° C. for two hours then cooled to room temperature. The tubing is removed, washed well with isopropanol and allowed to dry. The anhydride groups are then hydrolyzed with methanolic sodium hydroxide and dried in vacuo at 50° C.

EXAMPLE 9

The procedure of Example 8 is repeated but using natural rubber uretheral catheters, eustachian catheters or bladder catheters in place of the rubber tubing employed therein. The resulting catheters have reduced friction to human skin and are inserted into patients with significantly less difficulty than their untreated counterparts.

I claim:

1. A process for grafting a hydrophilic polymer of a carboxylic acid, or a salt thereof, onto the surface of a natural rubber article, said rubber article being selected from the group consisting of a sheet, glove and tube; and said acid being selected from the group consisting of maleic, acrylic, methacrylic, itaconic and citraconic acid; which comprises the steps of
    (a) contacting said rubber article with from 2 to 45 parts by weight, per part by weight of said rubber article, of an anhydride of said carboxylic acid, and 0.4 to 10 percent, based on weight of said anhydride, of a free radical polymerization initiator, at a temperature of from 50° to 150° C., in the presence of a reaction inert organic solvent which dissolves at least substantial portions of said monomeric acid anhydride and said initiator, and has no significant detrimental effect on the starting rubber article or product;
    (b) washing the resulting rubber article with a water miscible solvent to remove by-products and unreacted starting materials, followed by
    (c) hydrolysis of the washed article under aqueous alkaline conditions to convert carboxylic acid anhydride groups to carboxylate salts, and when free carboxylic acid groups are desired, acidifying with dilute aqueous or alcoholic acid.

2. A process according to claim 1 wherein said carboxylic acid is maleic acid.

3. A process according to claim 1 wherein said tube is a catheter.

4. A process according to claim 3 when carried out in the presence of an inert gas.

5. A process according to claim 1 wherein said solvent is chlorobenzene.

6. A process according to claim 1 wherein said initiator is t-butyl peroctoate.

7. A process according to claim 6 wherein said initiator is employed at 2-6 percent based on the weight of acid anhydride.

8. A process according to claim 1 wherein said temperature is from 90° to 110° C.

9. A process according to claim 1 wherein said water miscible solvent is acetone.

10. A process according to claim 1 wherein the hydrolysis step is carried out in the presence of an alkali metal hydroxide.

11. A process according to claim 10 wherein said alkali metal hydroxide is sodium hydroxide.

12. A process according to claim 11 wherein said hydrolysis is carried in aqueous dimethylformamide or aqueous dioxane.

13. A natural rubber article selected from the group consisting of a sheet, glove and tube, having a hydrophilic surface when prepared according to the process of claim 1.

14. A rubber glove according to claim 13.

15. A rubber tube according to claim 13.

16. An article according to claim 15 wherein said tube is a catheter.

* * * * *

UNITED STATES PATENT AND TRADEMARK OFFICE
CERTIFICATE OF CORRECTION

PATENT NO. : 4,526,579
DATED : July 2, 1985
INVENTOR(S) : Parviz R. Ainpour

It is certified that error appears in the above-identified patent and that said Letters Patent is hereby corrected as shown below:

On the cover page, [73] Assignee:, "Pfizer Inc.," should read -- Howmedica, Inc., --.

Signed and Sealed this

Nineteenth Day of November 1985

[SEAL]

Attest:

Attesting Officer

DONALD J. QUIGG

Commissioner of Patents and Trademarks